US010128961B2

(12) United States Patent
Sekeljic et al.

(10) Patent No.: US 10,128,961 B2
(45) Date of Patent: Nov. 13, 2018

(54) ANGULAR ELECTRODE

(71) Applicant: Intel Corporation, Santa Clara, CA (US)

(72) Inventors: Nada Sekeljic, Hillsboro, OR (US); Anand S. Konanur, San Jose, CA (US); Timothy F. Cox, Palo Alto, CA (US); Suraj Sindia, Hillsboro, OR (US); John M. Roman, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/473,941

(22) Filed: Mar. 30, 2017

(65) Prior Publication Data

US 2018/0287715 A1    Oct. 4, 2018

(51) Int. Cl.
| | |
|---|---|
| *H04B 13/00* | (2006.01) |
| *A41D 1/00* | (2018.01) |
| *A41D 1/06* | (2006.01) |
| *A41D 27/10* | (2006.01) |
| *A43B 3/00* | (2006.01) |
| *A43B 23/02* | (2006.01) |
| *A43B 13/14* | (2006.01) |

(52) U.S. Cl.
CPC ........... *H04B 13/005* (2013.01); *A41D 1/002* (2013.01); *A41D 1/06* (2013.01); *A41D 27/10* (2013.01); *A43B 3/0005* (2013.01); *A43B 13/14* (2013.01); *A43B 23/0245* (2013.01)

(58) Field of Classification Search
CPC ........ H04B 13/005; A41D 1/002; A41D 1/06; A41D 27/10; A43B 3/0005; A43B 13/14; A43B 23/0245

USPC .................................. 455/41.1–41.3, 26.1
See application file for complete search history.

(56) References Cited

U.S. PATENT DOCUMENTS

| | | | |
|---|---|---|---|
| 6,216,545 B1 | 4/2001 | Taylor | |
| 8,633,809 B2 * | 1/2014 | Schenk | A61B 5/0024 340/286.01 |
| 9,627,777 B2 * | 4/2017 | Benzel | H01Q 13/085 |
| 9,641,261 B2 * | 5/2017 | Ying | H04B 13/005 |
| 2004/0219890 A1 * | 11/2004 | Williams | H04Q 9/04 455/100 |
| 2007/0140120 A1 * | 6/2007 | Song | H04B 13/005 370/230 |
| 2009/0004982 A1 * | 1/2009 | Kim | A61B 1/00016 455/128 |
| 2009/0231141 A1 * | 9/2009 | Kuo | G06K 19/07749 340/572.7 |
| 2010/0063779 A1 | 3/2010 | Schrock et al. | |

(Continued)

FOREIGN PATENT DOCUMENTS

KR           101128215 B1    3/2012

OTHER PUBLICATIONS

Zimmerman, T; "Personal Area Networks (PAN): Near-Field Intra-Body Communication"; IBM Systems Journal, vol. 35, No. 3.4; Publication [online]. 1996 [retrieved Mar. 22, 2018].

(Continued)

*Primary Examiner* — Fayyaz Alam
(74) *Attorney, Agent, or Firm* — Schiff Hardin LLP

(57) ABSTRACT

An electrode having a first metallic plate; and a second metallic plate arranged at an angle of greater than 0° and less than 180° with respect to the first metallic plate.

22 Claims, 5 Drawing Sheets

(56) References Cited

U.S. PATENT DOCUMENTS

| | | | |
|---|---|---|---|
| 2010/0105323 A1* | 4/2010 | Kawano | H04B 13/005 455/41.1 |
| 2010/0315206 A1* | 12/2010 | Schenk | H04B 13/005 340/286.01 |
| 2011/0286722 A1* | 11/2011 | Kim | A61B 1/00016 386/353 |
| 2012/0178387 A1* | 7/2012 | Ohishi | H01Q 1/273 455/90.2 |
| 2013/0027267 A1* | 1/2013 | Homan | A61B 1/00016 343/810 |
| 2014/0070957 A1* | 3/2014 | Longinotti-Buitoni | A61B 5/02055 340/870.01 |
| 2015/0018721 A1 | 1/2015 | Wang et al. | |
| 2016/0301482 A1* | 10/2016 | Konanur | H04B 13/005 |
| 2017/0111123 A1* | 4/2017 | Ouzounov | H04B 13/005 |
| 2017/0272176 A1* | 9/2017 | Konanur | H04B 13/005 |
| 2018/0076864 A1* | 3/2018 | Jan | H04B 7/0469 |

OTHER PUBLICATIONS

Search Report dated Mar. 22, 2018 for International Application No. PCT/US18/14667.

* cited by examiner

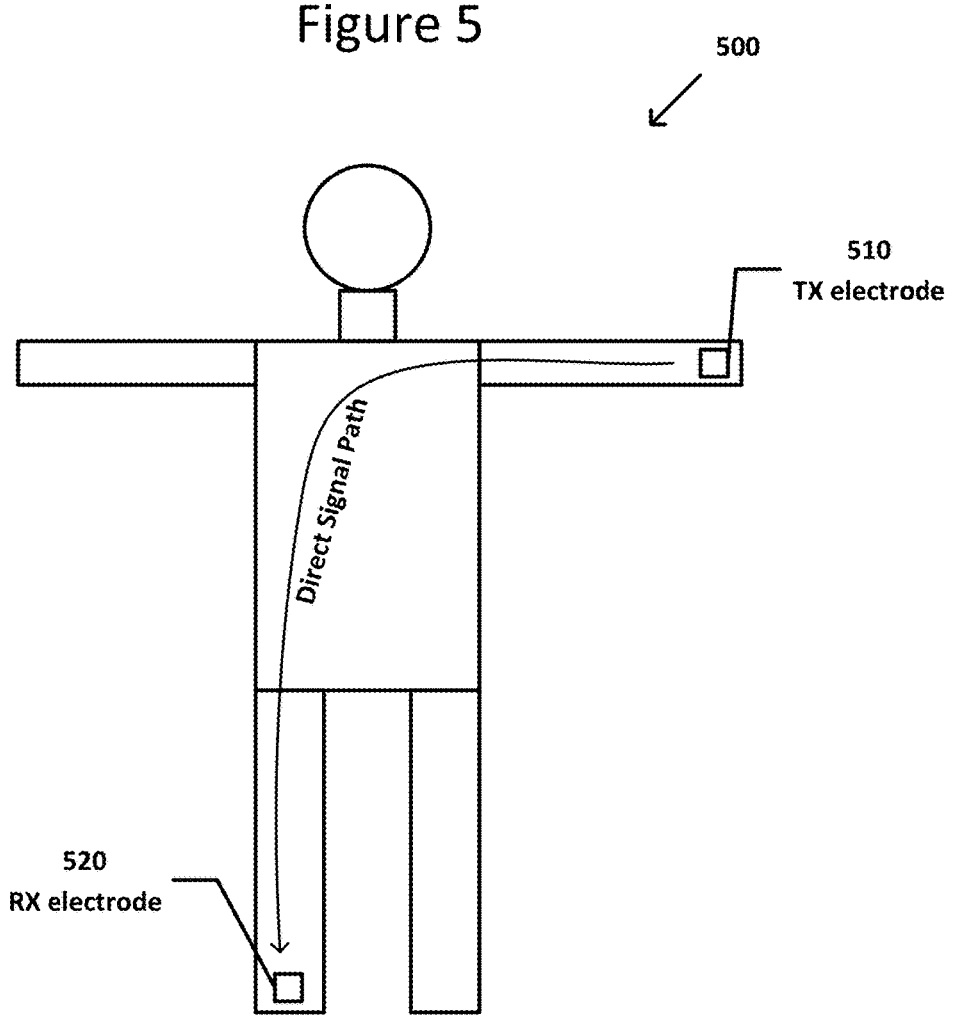

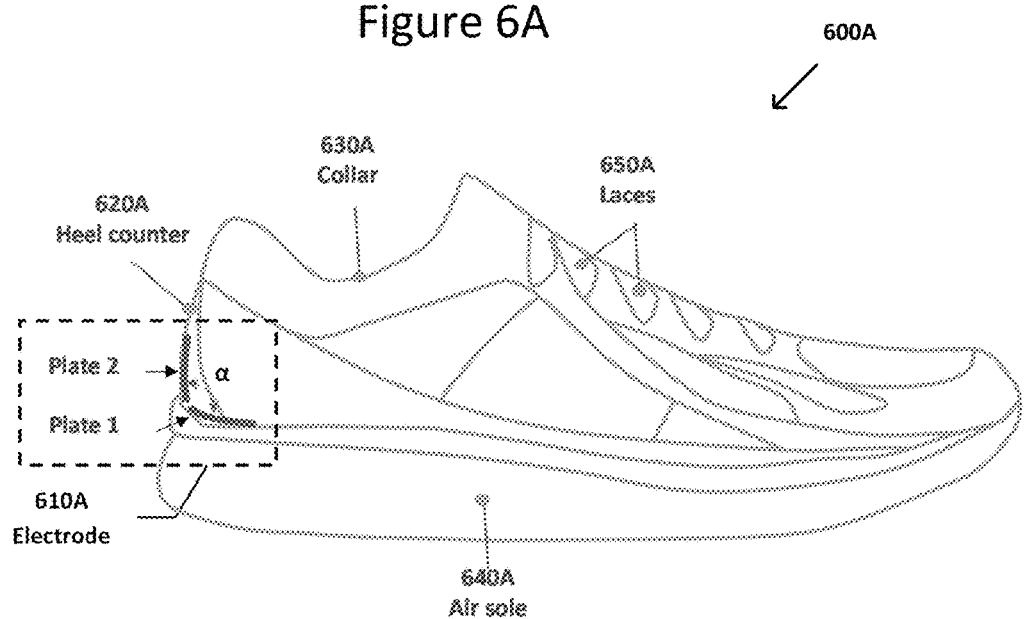
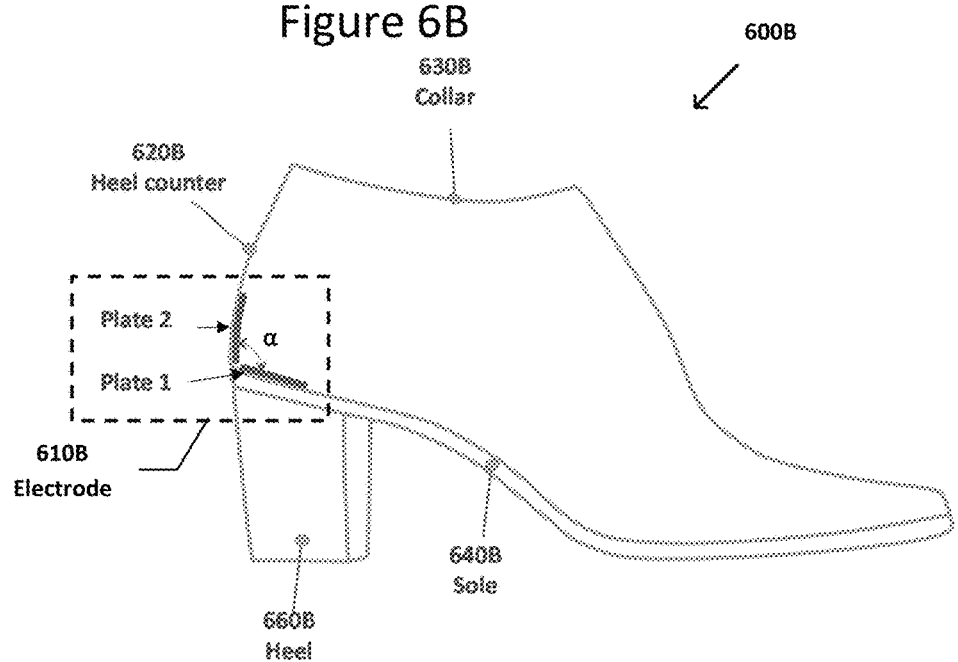

ANGULAR ELECTRODE

BACKGROUND

The present disclosure generally relates to an angular electrode, and more specifically, to an angular electrode of a Human Body Communication Networks (HBCN), otherwise known as Wireless Body Area Networks (WBAN).

HBCN/WBAN is an emerging technology based on low power, short range signal propagation. As opposed to Radio Frequency (RF) networks in which a signal propagates through the air, an HBCN/WBAN channel is established through a human body due to the high conductivity of human tissue. In order to send and receive signals via the HBCN/WBAN channel, electrodes are attached to, or positioned in its close proximity to, the human body. Electrode design thus has an important role in HBCN/WBAN channel characterization in terms of path loss, signal-to-noise (SNR) ratio, and data speed.

An HBCN/WBAN operates in the lower Radio Frequency (RF) range, for example, below 100 MHz, and is based on near Electro-Magnetic Field (EMF) coupling between human body tissue and the environment by an electrode. Electrode design for this frequency range is a challenging task because electrodes are electrically small as compared to the wavelength of the propagating signal, and their radiation efficiency is relatively low.

BRIEF DESCRIPTION OF THE DRAWINGS

FIG. 5 illustrates a schematic diagram of a wrist-ankle HBCN/WBAN link in accordance with an aspect of the disclosure.

FIG. 6A illustrates a running footwear having an angular electrode in accordance with an aspect of the disclosure.

FIG. 6B illustrates a high-heel fashion footwear having an angular electrode in accordance with an aspect of the disclosure.

DESCRIPTION OF THE ASPECTS

The present disclosure is directed to an electrode having a first metallic plate, and a second metallic plate arranged at an angle of greater than 0° and less than 180° with respect to the first metallic plate.

This angular electrode may be used, for example, in smart footwear wireless communication as a part of a Human Body Communication Network (HBCN), otherwise known as Wireless Body Area Network (WBAN). The angular electrode, as opposed to a previous vertical stack-up electrode, improves signal path loss of an HBCN/WBAN link, and is also more suitable for a smart footwear design.

Figure 1:
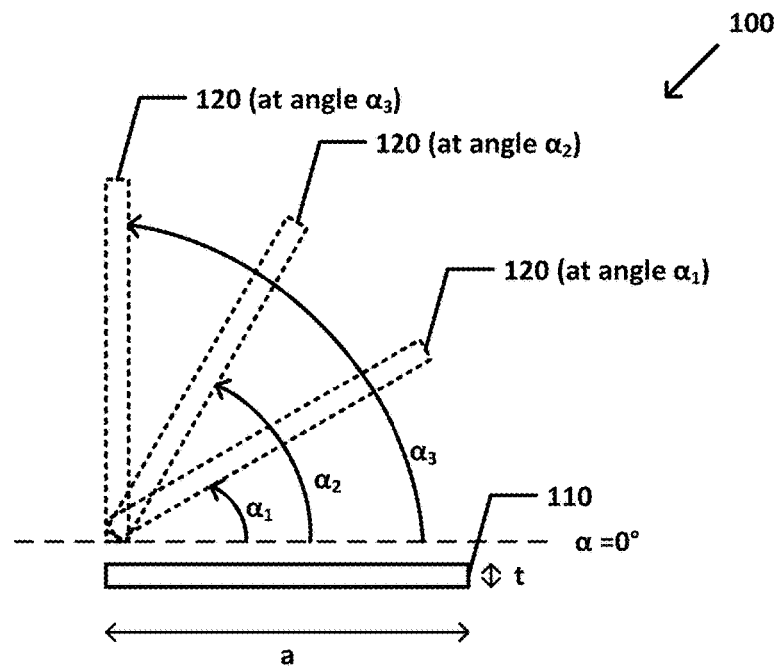
FIG. 1 illustrates a schematic diagram of an angular electrode in accordance with an aspect of the disclosure.

FIG. 1 illustrates a schematic diagram of an angular electrode 100 in accordance with an aspect of the disclosure.

The angular electrode 100 comprises a first metallic plate 110, and a second metallic plate 120. The second metallic plate 120 may be arranged at any angle of greater than 0° and less than 180° with respect to the first metallic plate 110. The first and second metallic plates 110, 120 may comprise copper, or any other suitable metal or combination of metals. Also, each of the first and second metallic plates 110, 120 may be formed to be straight or curved, as suitable for a particular application. The curve may be convex or concave. The first and second metallic plates 110 and 120 may have different shapes from one another in any combination (e.g., straight-straight, curved-curved, concave-concave, convex-convex, concave-convex, straight-curved (concave or convex)), etc. In a case of a curved metallic plate, the angle of the curved metallic plate relative to another metallic plate is based on a tangent drawn at a maximum curvature of the curved metallic plate.

When the angular electrode 100 is comprised within an application setting, a dielectric material (not shown) is located between the first and second metallic plates 110, 120. This dielectric may be, for example, animal tissue, body tissue, air, plastic, or any other material have a dielectric constant within a range suitable for the intended application.

The second metallic plate 120 is shown at three possible angles ($\alpha_1$, $\alpha_2$, and $\alpha_3$) that are at 90° or less with respect to the first metallic plate 110. A best angle performance-wise is angle $\alpha_3$, which is 90°, or L-shaped. Each of angles $\alpha_1$ and $\alpha_2$ is between 0° and 90°.

The angular electrode 100 is an attractive design for smart footwear applications used in, for example, fitness and healthcare. The shape, length a, and thickness t of the metallic plates 110 120, as well as the angle $\alpha$, depends on footwear style and anatomy. With this degree of freedom, the angular electrode 110 can be designed to conform to a shape of a footwear. Also, there are no restrictions as to where the angular electrode can be embedded inside the footwear. The design of the angular electrode 100 is optimized based on EMF analysis of the HBCN/WBAN link established between an electrode acting as a transmitter (TX) and an electrode acting as a receiver (RX), one of which may be attached to a human forearm.

Figure 2:
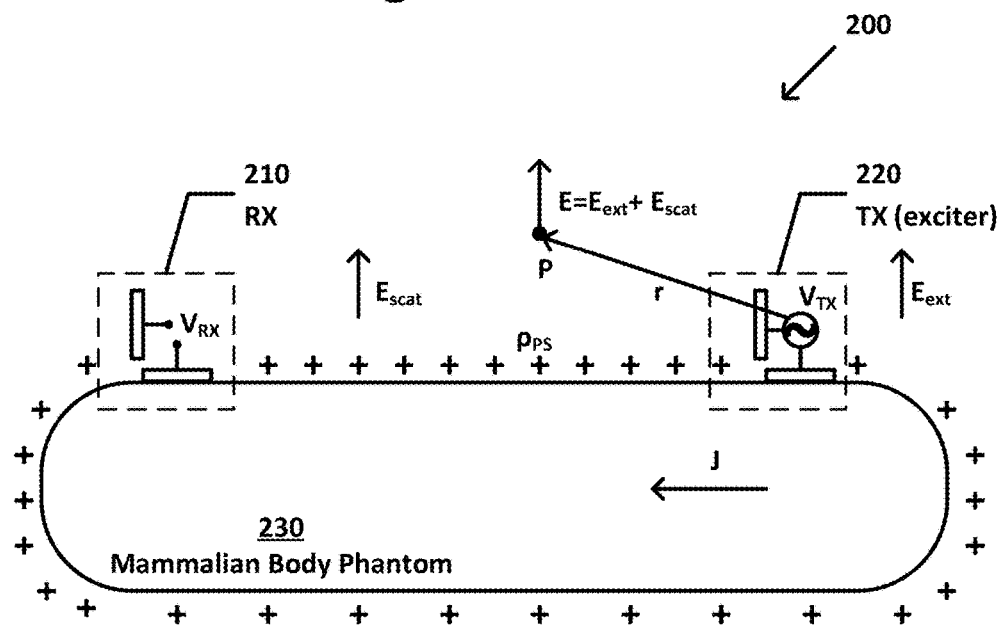
FIG. 2 illustrates an electromagnetic diagram of an HBCN/WBAN link established between two electrodes coupled to human body tissue in accordance with an aspect of the disclosure.

FIG. 2 illustrates an EM diagram 200 of an HBCN/WBAN link established between two electrodes coupled to human body tissue in accordance with an aspect of the disclosure.

The EM diagram 200 comprises a receiver electrode 210, a transmitter electrode 220, and human body tissue 230, or any other similar tissue that can act as a dielectric.

When a human body, which is a lossy conductor, is exposed to an external time-varying field $E_{ext}$ generated by an exciter (transmitter electrode 220), surface polarization charges $\rho_{PS}$ are induced on the body surface, and volume current density J is induced in the body 230. These induced sources emit from the body 230 a scattered field $E_{scat}$. The total field E, which is the superposition of the external and scattered fields, can be computed at any point P at a radial distance r from the exciter 220 by solving a second order partial differential equation known as the vector wave equation:

$$\nabla \times \mu_r^{-1} \nabla \times E - \varepsilon_r k_0^2 E = 0 \qquad \text{(Equation 1)}$$

where $\mu_r$ is the relative permeability and $\varepsilon_r$ is the relative permittivity of the medium, and $k_0$ is the phase coefficient of the propagating wave. A potential difference generated by an electric field distribution can be measured with an electrode. The quality of the measured signal depends largely on the electrode design.

A received voltage $V_{RX}$, which can be computed as the line integral of electric field, is adopted to evaluate system in accordance with the following equation:

$$V_{RX} = \int_L E \cdot dl \qquad \text{(Equation 2)}$$

where L is the integration line.

The Path Loss (PL) in dB is calculated based on a ratio of received voltage $V_{RX}$ to transmitted voltage $V_{TX}$ in accordance with the following equation:

$$PL[\text{dB}] = -20\log_{10}\frac{V_{RX}}{V_{TX}} \qquad \text{(Equation 3)}$$

Improving the signal path loss can lead to an improved Signal-to-Noise Ratio (SNR) and higher data speed in the HBCN/WBAN link, while an optimal angular design can fit inside the smart footwear better without affecting footwear size and fashion style. For instance, previously suggested solutions, such as the vertical stack-up electrode, can affect the thickness of the footwear sole, limiting the applications to footwear which usually have a thicker air sole. The angular electrode disclosed herein can be incorporated into any footwear. In addition to the optimal angular design, improved signal path loss has many wireless communications system benefits. Also, since the bandwidth and receiver noise are fixed, reduction of transmit signal power can be realized. This allows for a lower power solution that is desirable in the wearable market.

Figure 3:
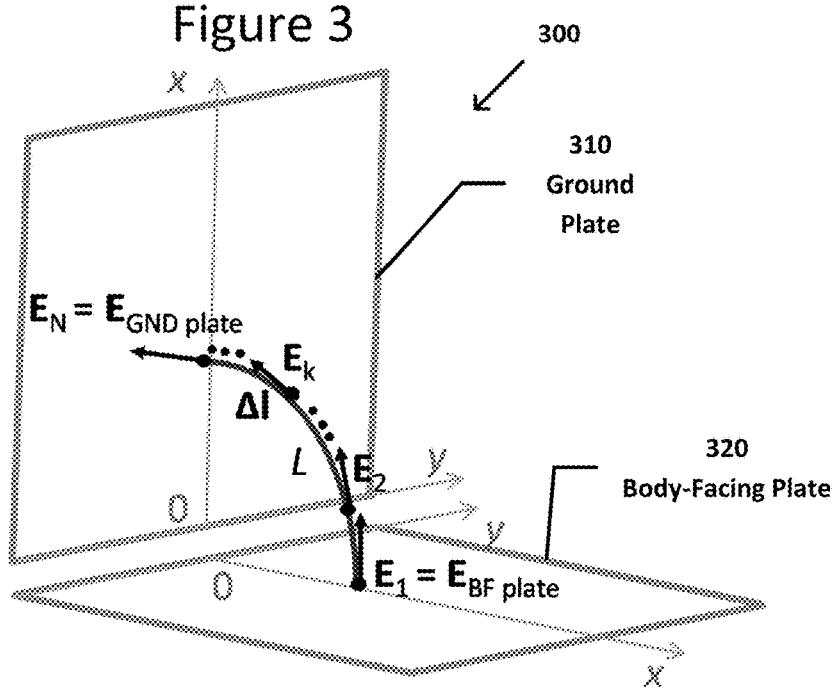
FIG. 3 illustrates a schematic diagram of an L-shaped electrode in accordance with an aspect of the disclosure.

FIG. 3 illustrates a schematic diagram of an L-shaped electrode 300 in accordance with an aspect of the disclosure.

Human body communication is established between two electrodes 300 located on or close to the body and having a dielectric therebetween. One electrode 300 acts as transmitter and the other electrode 300 acts as receiver. Each electrode 300 comprises two metallic plates—a ground plate 310 floating in the air, and a body-facing (BF) plate 320 attached or located close to the human body. The ground plate 310 couples the signal with the environment (secondary signal path) and BF plate 320 couples the signal through the body (primary or direct signal path). The transmit and receive electrodes 300, which may comprise copper ($\sigma_{Cu}$=58 MS/m), may be coupled to a human forearm.

The L-shaped electrode 300, compared with previous vertical stack-up designs, results in a higher potential difference between the body-facing plate 320 and the ground plate 310. Also, there is a stronger electric field (E-field) due to stronger surface charge density accumulated at the corner of the electrode 300.

The voltage (measured signal) between two plates of an electrode 300 can be evaluated using Equation 2 above, which in a practical case can be written as follows:

$$V_{RX} = \int_L E \cdot dl \approx \sum_{k=1}^{N} E_k \Delta l \qquad \text{(Equation 4)}$$

where L is the integration line subdivided into N differential increments of uniform length $\Delta l$, and $E_k$ is the intensity of the tangential component of E-field on the kth interval.

The L-shaped configuration generates an E-field approximately ten times stronger at the corner as compared to a vertical stack-up configuration, which behaves as a parallel plate capacitor with almost uniform field between two plates.

Figure 4:
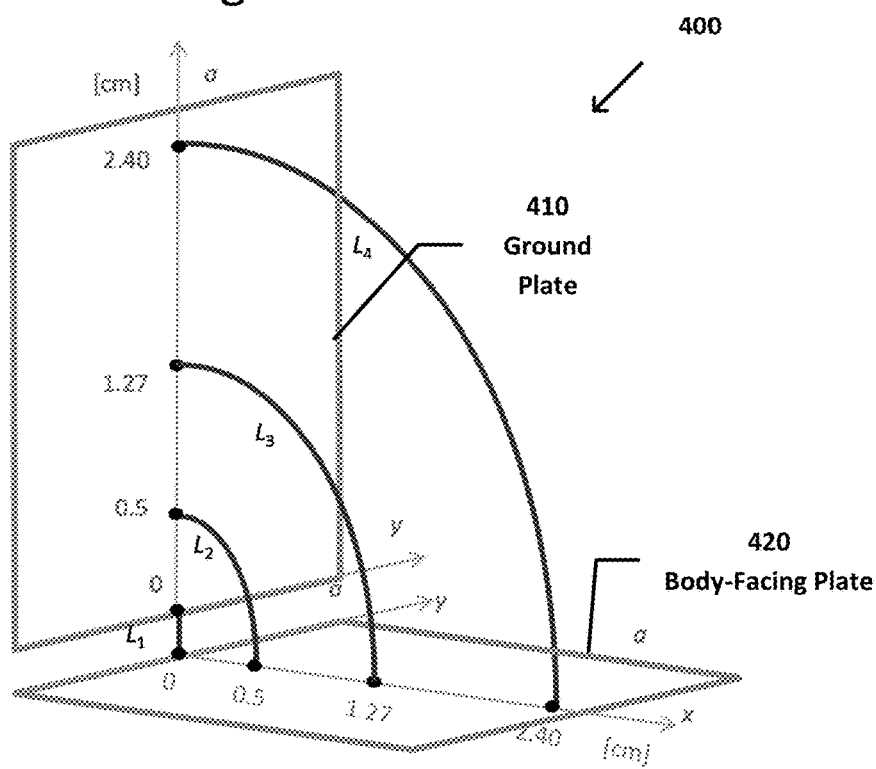
FIG. 4 illustrates a schematic diagram of an L-shaped electrode with integration lines in accordance with an aspect of the disclosure.

FIG. 4 illustrates a schematic diagram of an L-shaped electrode 400 with integration lines in accordance with an aspect of the disclosure.

The L-shaped electrode 400 is shown with four different integration lines, L1 to L4. The output voltage will not change significantly with respect to choice of integration line due to slowly-varying E-field. From a measurement standpoint and practical port definition, L1 is the optimal choice for an integration line.

FIG. 5 illustrates a schematic diagram of a wrist-ankle HBCN/WBAN link 500 in accordance with an aspect of the disclosure.

A transmit electrode 510 is attached to an arm/wrist or within a forearm device, and a receive electrode 520 is attached to the opposite leg ankle. Alternatively, the receive electrode 520 may be comprised within a footwear, as discussed further below with respect to FIGS. 6A, 6B, 7A, and 7B. The HBCN/WBAN link (direct signal path) is extended to a whole-body phantom.

FIG. 6A illustrates a running footwear 600A having an angular electrode in accordance with an aspect of the disclosure.

The running footwear 600A comprises an angular electrode 610A, a heel counter 620A, a collar 630A, an air sole 640A, and laces 650A. An "upper" is defined as the entire portion of the running footwear 600A that covers the foot.

The angular electrode 610A is located in a corner of a heel region of the upper, and is conformal to the heel counter 620A. The angular electrode 610A comprises metallic plate 1 and metallic plate 2 positioned at an angle α with respect to each other, and the angle α faces in an upward direction. When the running footwear 600A is worn, the wearer's heel, with or without a sock, is located in the angle between the plates 1 and 2 and acts as a dielectric.

The metallic plates 1 and 2 may be formed to be straight or curved, but in this case is more ideally curved to follow the curve of the heel counter 620A. As stated above, the curve may be convex or concave. In a case of a curved metallic plate, the angle of the curved metallic plate relative to another metallic plate is based on a tangent drawn at a maximum curvature of the curved metallic plate. Also, the two metallic plates 1 and 2 may have different shapes from one another in any combination. The electrode configuration is ideally as thin as possible in order not to impact footwear style or cause any discomfort.

FIG. 6B illustrates a high-heel fashion footwear 600B having an angular electrode in accordance with an aspect of the disclosure.

The footwear 600B comprises an angular electrode 610B, a heel counter 620B, a collar 630B, a sole 640B, and a heel 660B. Again, an "upper" is defined as the entire portion of the running footwear 600B that covers the foot.

The angular electrode 610B is located in a corner of a heel region of the upper and conformal to the heel counter 620B. The angular electrode 610B comprises metallic plate 1 and metallic plate 2 positioned at an angle α with respect to each other, and the angle α faces in an upward direction. When the footwear 600B is worn, the wearer's heel, with or without a sock, is located in the angle between the plates 1 and 2 and acts as a dielectric.

The metallic plates 1 and 2 may be formed to be straight or curved, but in this case is more ideally curved to follow the curve of the heel counter 620B. The curve may be convex or concave, and the two metallic plates 1 and 2 may have different shapes from one another in any combination. The electrode configuration is ideally as thin as possible in order not to impact footwear style or cause any discomfort.

Figure 7A:
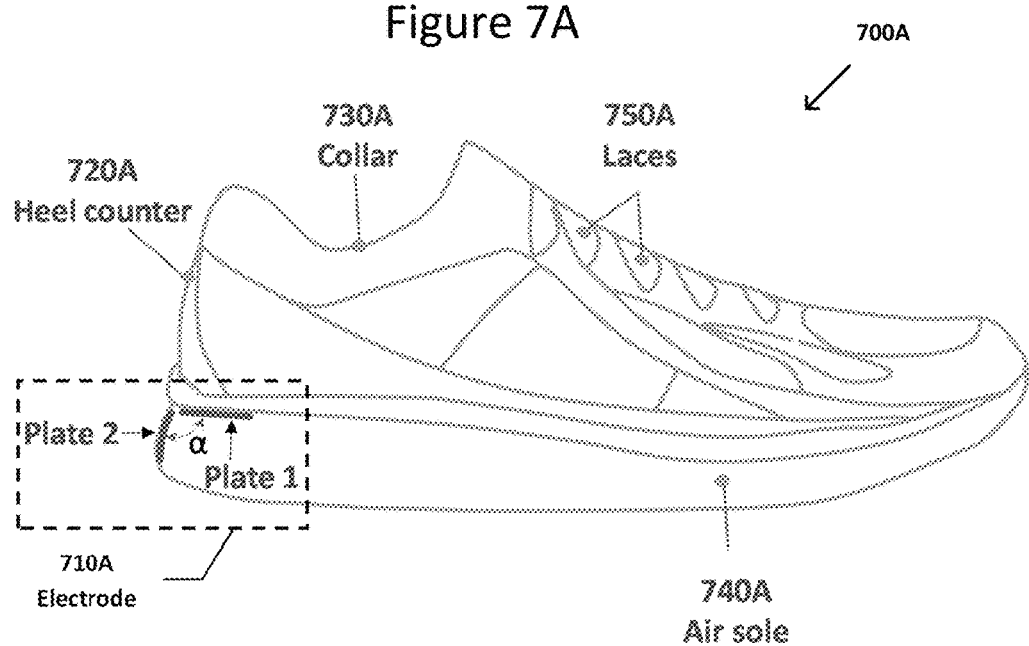
FIG. 7A illustrates a running footwear having an angular electrode in accordance with another aspect of the disclosure.

FIG. 7A illustrates a running footwear 700A having an angular electrode in accordance with another aspect of the disclosure.

The running footwear 700A comprises an angular electrode 710A, a heel counter 720A, a collar 730A, an air sole 740A, and laces 750A. Again, an "upper" is defined as the entire portion of the running footwear 700A that covers the foot.

The angular electrode 710A is incorporated in the air sole 740A at a corner where the air sole 740A joins the heel counter 720A of the upper. The angular electrode 710A comprises metallic plate 1 and metallic plate 2 positioned at an angle α with respect to each other, and the angle α faces in a downward direction. Between the metallic plates 1 and 2 may be air or a material having appropriate dielectric properties. The metallic plates 1 and 2 may be formed to be straight or curved. The curve may be convex or concave, and the two metallic plates 1 and 2 may have different shapes from one another in any combination.

Figure 7B:
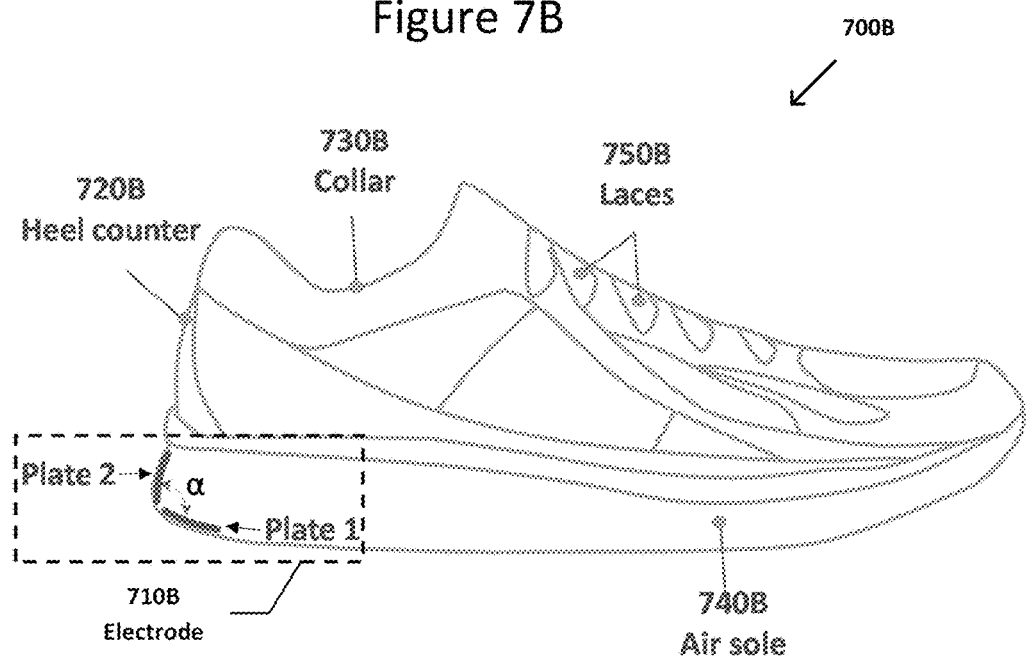
FIG. 7B illustrates a running footwear having an angular electrode in accordance with another aspect of the disclosure.

FIG. 7B illustrates a running footwear 700B having an angular electrode in accordance with another aspect of the disclosure.

The running footwear 700B comprises an angular electrode 710B, a heel counter 720B, a collar 730B, an air sole 740B, and laces 750B. Again, an "upper" is defined as the entire portion of the running footwear 700B that covers the foot.

The angular electrode 710B is incorporated in the air sole 740B at a bottom corner where the air sole 740B is designed to contact the ground during wear. The angular electrode 710B comprises metallic plate 1 and metallic plate 2 positioned at an angle α with respect to each other, and tin this case the angle α faces in an upward direction. Between the metallic plates 1 and 2 may be air or a material having appropriate dielectric properties. The metallic plates 1 and 2 may be formed to be straight or curved. The curve may be convex or concave, and the two metallic plates 1 and 2 may have different shapes from one another in any combination.

The disclosure is not limited to being applicable to a human body. The angular electrode is applicable to any material that may transmit current, such as human body tissue, animal tissue, or even fabric. In the case of fabric, the angular electrode may be located within a sleeve or leg of a garment, for example.

Also, the disclosure is not limited to both of the transmit electrode and the receive electrode being a angular electrode. One electrode may be an angular electrode, and the other electrode may be a different electrode, such as a vertical stack-up electrode.

The angular electrode as disclosed herein is advantageous over the previous vertical stack-up electrode configurations. For a comparable electrode size, an angular electrode improves signal path loss due to a more strongly coupled electric field, and increases reliability of data. This means that the size of the angular electrode can be reduced, with similar or greater performance than the previously suggested electrodes.

Previous vertical stack-up electrode configurations need to be large in order to provide a detectable signal. Also, once integrated with radio frequency circuitry, vertical stack-up electrode configurations are not optimal for smart footwear applications due to their cumbersome design which can affect footwear size and style. The angular electrode design is more suitable to be embedded inside a footwear, as the electrode geometry lends itself to footwear design. The electrode disclosed herein increases comfort to the wearer, and minimizes overall impact to footwear design.

The disclosure also includes the following examples.

Example 1 is an electrode, comprising: a first metallic plate; and a second metallic plate arranged at an angle of greater than 0° and less than 180° with respect to the first metallic plate.

Example 2 comprising the subject matter of Example 1, wherein each of the first and second metallic plates is formed to be straight.

Example 3 comprising the subject matter of Example 1, wherein at least one of the first and second metallic plates is formed to be curved.

Example 4 comprising the subject matter of Example 3, wherein each of the first and second metallic plates is formed to be curved.

Example 5 comprising the subject matter of Example 3, wherein the other of the first and second metallic plates is formed to be straight.

Example 6 comprising the subject matter of Example 3, wherein the at least one of the first and second metallic plates is formed to be convex with respect to the other of the first and second metallic plates.

Example 7 comprising the subject matter of Example 3, wherein the at least one of the first and second metallic plates is formed to be concave with respect to the other of the first and second metallic plates.

Example 8 comprising the subject matter of Example 3, wherein the at least one of the first and second metallic plates is formed to be concave with respect to the other of the first and second metallic plates, and the other of the first and second metallic plates is formed to be convex with respect to the at least one of the first and second metallic plates.

Example 9 comprising the subject matter of Example 1, wherein the second metallic plate is arranged at an angle of 90° with respect to the first plate.

Example 10 comprising the subject matter of Example 1, wherein the second metallic plate is arranged at an angle of less than 90° with respect to the first plate.

Example 11 comprising the subject matter of Example 1, wherein during operation: the first metallic plate is a ground plate floating with respect to human body tissue; and the second metallic plate is a body-facing plate in direct or indirect contact with the human body tissue.

Example 12 is a footwear, comprising: an upper; and the electrode of Example 1 arranged in a corner of a heel region of the upper.

Example 13 comprising the subject matter of Example 12, wherein the electrode is arranged within the upper such that the angle between the first and second metallic plates faces in an upward direction, and the electrode is formed to conform to a heel counter of the upper.

Example 14 is a footwear, comprising: an upper; a sole attached to the upper; and the electrode of Example 1 arranged within the sole and at a heel region of the sole.

Example 15 comprising the subject matter of Example 14, wherein the electrode is arranged within the sole such that the angle between the first and second metallic plates faces in a downward direction.

Example 16 comprising the subject matter of Example 14, wherein the electrode is arranged within the sole such that the angle between the first and second metallic plates faces in an upward direction.

Example 17 is an electrode pair of a Wireless Body Area Network (WBAN), the electrode pair comprising: a receiver electrode comprising: the electrode of claim Example 1; and a transmitter electrode comprising: a third metallic plate; and a fourth metallic plate, wherein during operation of the WBAN a signal path between the transmitter and receiver electrodes is through human body tissue.

Example 18 comprising the subject matter of Example 17, wherein the third metallic plate is arranged at an angle of greater than 0° and less than 180° with respect to the fourth metallic plate.

Example 19 comprising the subject matter of Example 17, wherein the third metallic plate is arranged at an angle of 90° with respect to the fourth metallic plate.

Example 20 comprising the subject matter of Example 17, wherein the third metallic plate is arranged to be parallel with respect to the fourth metallic plate in a vertical stack-up configuration.

Example 21 comprising the subject matter of Example 17, wherein the signal path is generated based on an electric field comprised of charges induced on a surface of the human body tissue and induced volume current within the human body tissue.

Example 22 comprising the subject matter of Example 17, wherein the transmitter electrode is comprised within a forearm device, and the receiver electrode is comprised within a footwear.

Example 23 comprising the subject matter of Example 17, wherein at least one of the receiver electrode and the transmit electrode is comprised within fabric.

Example 24 comprising the subject matter of Example 17, wherein the fabric is a sleeve of a shirt.

Example 25 comprising the subject matter of Example 17, wherein the fabric is a leg of a pair of pants.

Example 26 is an electrode pair of a Wireless Body Area Network (WBAN), the electrode pair comprising: a receiver electrode comprising: the electrode of any of Examples 1-13; and a transmitter electrode comprising: a third metallic plate; and a fourth metallic plate, wherein during operation of the WBAN a signal path between the transmitter and receiver electrodes is through human body tissue.

Example 27 comprising the subject matter of Example 26, wherein the third metallic plate is arranged at an angle of greater than 0° and less than 180° with respect to the fourth metallic plate.

Example 28 comprising the subject matter of Example 26, wherein the third metallic plate is arranged at an angle of 90° with respect to the fourth metallic plate.

Example 29 comprising the subject matter of Example 26, wherein the third metallic plate is arranged to be parallel with respect to the fourth metallic plate in a vertical stack-up configuration.

Example 30 comprising the subject matter of Example 26, wherein the signal path is generated based on an electric field comprised of charges induced on a surface of the human body tissue and induced volume current within the human body tissue.

Example 31 comprising the subject matter of Example 26, wherein the transmitter electrode is comprised within a forearm device, and the receiver electrode is comprised within a footwear.

Example 32 comprising the subject matter of Example 26, wherein at least one of the receiver electrode and the transmit electrode is comprised within fabric.

Example 33 comprising the subject matter of Example 26, wherein the fabric is a sleeve of a shirt.

Example 34 comprising the subject matter of Example 26, wherein the fabric is a leg of a pair of pants.

While the foregoing has been described in conjunction with exemplary aspect, it is understood that the term "exemplary" is merely meant as an example, rather than the best or optimal. Accordingly, the disclosure is intended to cover alternatives, modifications and equivalents, which may be included within the scope of the disclosure.

Although specific aspects have been illustrated and described herein, it will be appreciated by those of ordinary skill in the art that a variety of alternate and/or equivalent implementations may be substituted for the specific aspects shown and described without departing from the scope of the present application. This application is intended to cover any adaptations or variations of the specific aspects discussed herein.

The invention claimed is:

1. An electrode, comprising:
   a first metallic plate; and
   a second metallic plate arranged at an angle of greater than 0° and less than 180° with respect to the first metallic plate,
   wherein at least one of the first and second metallic plates is formed to maintain a curved planar surface.

2. The electrode of claim 1, wherein each of the first and second metallic plates is formed to maintain a curved planar surface.

3. The electrode of claim 1, wherein the other of the first and second metallic plates is formed to be straight.

4. The electrode of claim 1, wherein the at least one of the first and second metallic plates is formed to be convex with respect to the other of the first and second metallic plates.

5. The electrode of claim 1, wherein the at least one of the first and second metallic plates is formed to be concave with respect to the other of the first and second metallic plates.

6. The electrode of claim 1, wherein the at least one of the first and second metallic plates is formed to be concave with respect to the other of the first and second metallic plates, and the other of the first and second metallic plates is formed to be convex with respect to the at least one of the first and second metallic plates.

7. The electrode of claim 1, wherein the second metallic plate is arranged at an angle of less than 90° with respect to the first plate.

8. The electrode of claim 1, wherein during operation:
   the first metallic plate is a ground plate floating with respect to human body tissue; and
   the second metallic plate is a body-facing plate in direct or indirect contact with the human body tissue.

9. A footwear, comprising:
   an upper; and
   an electrode arranged in a corner of a heel region of the upper, the electrode comprising:
   a first metallic plate; and
   a second metallic plate arranged at an angle of greater than 0° and less than 180° with respect to the first metallic plate.

10. The footwear of claim 9, wherein the electrode is arranged within the upper such that the angle between the first and second metallic plates faces in an upward direction, and the electrode is formed to conform to a heel counter of the upper.

11. A footwear, comprising:
an upper;
a sole attached to the upper; and
an electrode arranged within the sole and at a heel region of the sole, the electrode comprising:
a first metallic plate; and
a second metallic plate arranged at an angle of greater than 0° and less than 180° with respect to the first metallic plate.

12. The footwear of claim 11, wherein the electrode is arranged within the sole such that the angle between the first and second metallic plates faces in a downward direction.

13. The footwear of claim 11, wherein the electrode is arranged within the sole such that the angle between the first and second metallic plates faces in an upward direction.

14. An electrode pair of a Wireless Body Area Network (WBAN), the electrode pair comprising:
a receiver electrode comprised within footwear and comprising:
an electrode comprising:
a first metallic plate; and
a second metallic plate arranged at an angle of greater than 0° and less than 180° with respect to the first metallic plate; and
a transmitter electrode comprised within a forearm device and comprising:
a third metallic plate; and
a fourth metallic plate,
wherein during operation of the WBAN a signal path between the transmitter and receiver electrodes is through human body tissue, and
wherein at least one of the receiver electrode and the transmit electrode is comprised within a fabric sleeve of a shirt or a fabric leg of a pair of pants.

15. The electrode pair of claim 14, wherein the third metallic plate is arranged at an angle of greater than 0° and less than 180° with respect to the fourth metallic plate.

16. The electrode pair of claim 14, wherein the third metallic plate is arranged at an angle of 90° with respect to the fourth metallic plate.

17. The electrode pair of claim 14, wherein the third metallic plate is arranged to be parallel with respect to the fourth metallic plate in a vertical stack-up configuration.

18. The electrode pair of claim 14, wherein the signal path is generated based on an electric field comprised of charges induced on a surface of the human body tissue and induced volume current within the human body tissue.

19. An electrode, comprising:
a first metallic plate; and
a second metallic plate arranged at an angle of greater than 0° and less than 90°, or greater than 90° and less than 180°, with respect to the first metallic plate,
wherein at least one of the first metallic plate and the second metallic plate has a curved planar surface.

20. The footwear of claim 9, wherein at least one of the first metallic plate and the second metallic plate has a curved planar surface.

21. The footwear of claim 11, wherein at least one of the first metallic plate and the second metallic plate has a curved planar surface.

22. The electrode pair of claim 14, wherein at least one of the first metallic plate and the second metallic plate has a curved planar surface.

* * * * *